US009939727B2

(12) United States Patent
Yamada

(10) Patent No.: US 9,939,727 B2
(45) Date of Patent: Apr. 10, 2018

(54) METHOD FOR MANUFACTURING PATTERNED OBJECT, PATTERNED OBJECT, AND LIGHT IRRADIATION APPARATUS

(71) Applicant: USHIO DENKI KABUSHIKI KAISHA, Tokyo (JP)

(72) Inventor: Go Yamada, Tokyo (JP)

(73) Assignee: USHIO DENKI KABUSHIKI KAISHA, Tokyo (JP)

(*) Notice: Subject to any disclaimer, the term of this patent is extended or adjusted under 35 U.S.C. 154(b) by 0 days.

(21) Appl. No.: 15/306,967

(22) PCT Filed: Oct. 6, 2015

(86) PCT No.: PCT/JP2015/005090
§ 371 (c)(1),
(2) Date: Oct. 26, 2016

(87) PCT Pub. No.: WO2016/056232
PCT Pub. Date: Apr. 14, 2016

(65) Prior Publication Data
US 2017/0052447 A1    Feb. 23, 2017

(30) Foreign Application Priority Data
Oct. 8, 2014    (JP) .................. 2014-207626

(51) Int. Cl.
G03F 7/20        (2006.01)
H01L 21/027      (2006.01)
(Continued)

(52) U.S. Cl.
CPC .......... G03F 7/2002 (2013.01); C07C 323/03 (2013.01); C07F 9/3808 (2013.01);
(Continued)

(58) Field of Classification Search
CPC .......... G03F 7/002; G03F 7/165; G03F 7/004; G03F 7/2004; G03F 7/2002; G03F 7/11;
(Continued)

(56) References Cited

U.S. PATENT DOCUMENTS 5,418,424 A      5/1995   Aprile et al.
2009/0079953 A1* 3/2009   French .................. G03F 7/2041
                                              355/71

(Continued)

FOREIGN PATENT DOCUMENTS

JP   2001-185076 A    7/2001
JP   2001-324819 A    11/2001
(Continued)

OTHER PUBLICATIONS

Machine translation of JP 2001-324816 (no date).*
(Continued)

Primary Examiner — Amanda C Walke
(74) Attorney, Agent, or Firm — Studebaker & Brackett PC

(57) ABSTRACT

Disclosed herein is a method for manufacturing a patterned object and a light irradiation apparatus that make it possible to form a pattern that accurately follows a mask pattern with higher accuracy in a patterning process of irradiating a pattern forming substrate with vacuum ultra violet light. The light irradiation apparatus includes a mask stage arranged apart from the pattern forming substrate and configured to hold a mask on which a prescribed pattern is formed, and a vacuum ultra violet light source unit configured to irradiate the pattern forming substrate with vacuum ultra violet light through the mask. A space between the mask and the pattern forming substrate is set to be an atmosphere containing oxygen. The vacuum ultra violet light source unit irradiates light, as the vacuum ultra violet light, having a continuous spectrum in a range where a wavelength ranges from 180 nm to 200 nm.

8 Claims, 7 Drawing Sheets

(51) Int. Cl.
  *G03F 7/16* (2006.01)
  *C07F 9/38* (2006.01)
  *C07C 323/03* (2006.01)
  *G03F 7/00* (2006.01)
  *H01L 51/05* (2006.01)

(52) U.S. Cl.
  CPC .............. *G03F 7/002* (2013.01); *G03F 7/165* (2013.01); *G03F 7/2039* (2013.01); *G03F 7/7035* (2013.01); *H01L 21/0274* (2013.01); *H01L 51/052* (2013.01)

(58) Field of Classification Search
  CPC . G03F 7/70; G03F 2007/2067; C07C 323/03; C07F 9/3808
  USPC ........................................................ 430/322
  See application file for complete search history.

(56) References Cited

U.S. PATENT DOCUMENTS

| | | | | |
|---|---|---|---|---|
| 2011/0249243 | A1* | 10/2011 | Sjmaenok | G03F 7/70191 355/18 |
| 2012/0226070 | A1* | 9/2012 | Isono | C07C 69/653 560/197 |
| 2013/0209938 | A1* | 8/2013 | Takihana | C07C 309/10 430/285.1 |
| 2014/0361196 | A1* | 12/2014 | Owada | H01J 21/02 250/492.1 |
| 2015/0235911 | A1* | 8/2015 | Asano | B05C 21/005 438/7 |
| 2016/0155986 | A1* | 6/2016 | Ito | H01L 51/5253 257/734 |

FOREIGN PATENT DOCUMENTS

| | | |
|---|---|---|
| JP | 2009-244576 A | 10/2009 |
| JP | 5056538 B2 | 8/2012 |
| JP | 2015-126139 A | 7/2015 |
| WO | 35/02260 A1 | 1/1995 |
| WO | 2015/098392 A1 | 7/2015 |

OTHER PUBLICATIONS

Machine translation of JP 2015-126139 (no date).*
International Search Report issued in PCT/JP2015/005090, dated Dec. 22, 2015.

* cited by examiner

METHOD FOR MANUFACTURING PATTERNED OBJECT, PATTERNED OBJECT, AND LIGHT IRRADIATION APPARATUS

TECHNICAL FIELD

The present invention relates to a patterned object manufacturing method for manufacturing a patterned object through a patterning process using light including vacuum ultra violet light, a patterned object manufactured through such a manufacturing method, and a light irradiation apparatus.

BACKGROUND ART

In recent years, vacuum ultra violet (VUV) light having a wavelength of 200 nm or less is used in a variety of fields aside from the semiconductor exposure field. For example, a technique of patterning a self-assembled monolayers (SAM) by inducing a chemical reaction directly with light with the use of VUV and a mask, without using a pattern forming process with a photoresist, is being developed. A patterned SAM is used, for example, as a gate insulating film for an organic thin film transistor.

In addition, as a process for manufacturing a new device, there is a demand that a pattern having various functional properties, such as hydrophilicity, hydrophobicity, reactivity, and electrical interaction, be formed on an organic substrate by irradiating the substrate with the VUV light. A substrate on which such a pattern is to be formed is made, for example, of a cyclic olefin resin, such as a cyclic olefin polymer (COP) and a cyclic olefin copolymer (COC), and these are used, for example, in biofunctional microdevices, such as a biochip.

Methods of manufacturing a patterned object include, for example, a technique disclosed in PATENT LITERATURE 1 (Japanese Patent Publication No. 5056538 B). In this technique, a substrate on which a SAM is formed serves as a pattern forming substrate, and the SAM on this pattern forming substrate is irradiated with the VUV light via a mask so as to remove a portion of the SAM in a patterned shape. Here, the SAM is irradiated with the VUV light in the presence of a reactive gas containing at least oxygen. In addition, an excimer lamp or the like that emits excimer light having a main peak wavelength of 172 nm is used as a light source for emitting the VUV light.

LISTING OF REFERENCES

PATENT LITERATURE 1: Japanese Patent Publication No. 5056538 B

SUMMARY OF THE INVENTION

Problems to be Solved by the Invention

However, when an atmosphere containing oxygen is irradiated with the VUV light, oxygen is decomposed by the irradiated VUV light so that active oxygen, such as ozone or the like, is generated. In this regard, when a space between a mask and a SAM is an atmosphere containing oxygen, as in the technique disclosed in PATENT LITERATURE 1 (Japanese Patent Publication No. 5056538 B), active oxygen (or radical oxygen) is generated in this space through the irradiation with the VUV light. The active oxygen generated at this point flows into the portion on the SAM that is covered by the mask (that is, a non-exposure portion), and an oxidative decomposition reaction between the SAM and the active oxygen occurs in the non-exposure portion. As a result, a partial defect in the SAM caused by the active oxygen occurs, which leads to a deterioration in the accuracy of a pattern formed in the SAM.

In order to suppress generation of active oxygen that could cause such a deterioration in the pattern accuracy, a countermeasure that the entire irradiation atmosphere of the VUV light is purged with an inert gas is conceivable, but this countermeasure incurs an increase in the cost and is thus not preferable.

Taking the above mentioned circumstances into consideration, the present invention has been made in order to solve the above mentioned problems and an object thereof is to provide a method of manufacturing a patterned object, a patterned object, and a light irradiation apparatus that make it possible to form a pattern that accurately follows a mask pattern with higher accuracy in a patterning process of irradiating a pattern forming substrate with vacuum ultra violet light via a mask in an atmosphere containing oxygen.

Solution to Problems

In order to solve the above mentioned problems, according to one aspect of a method for manufacturing a patterned object of the present invention, there is provided a method for manufacturing a patterned object, comprising: irradiating a pattern forming substrate with light containing vacuum ultra violet light in an atmosphere containing oxygen via a mask on which a prescribed pattern is formed; and manufacturing a patterned object in which a pattern is formed including a modified portion and non-modified portion on a light irradiation surface of the pattern forming substrate. The vacuum ultra violet light is light having a continuous spectrum in a range where a wavelength ranges from 180 nm to 200 nm.

The inventor(s) of the present invention has conceived that, out of vacuum ultra violet light having the wavelength equal to or less than 200 nm used for an optical patterning, a light absorption significantly occurs by oxygen in the range of wavelength less than 180 nm, which is a short wavelength side, while a light absorption hardly occurs by oxygen in the range of wavelength from 180 nm to 200 nm (equal to or greater than 180 nm and equal to or less than 200 nm).

As described above, when the optical patterning is performed in an atmosphere containing oxygen, by using the vacuum ultra violet light (VUV light) having the wavelength in the range from 180 nm to 200 nm, it makes it possible to suppress, in particular, active oxygen (ozone or the like) from being generated in a space between the mask and the pattern forming substrate, and also suppress the generated active oxygen from flowing into a portion covered by a mask shielding portion (that is, non-exposure portion), as compared to the case in which short wavelength VUV light having a wavelength less than 180 nm is used. as a result, it makes it possible to suppress the surface modification from occurring by the active oxygen in the non-exposure portion of the pattern forming substrate.

In addition, as the concentration of the active oxygen in the space between the mask and the pattern forming substrate is lowered, it makes it possible to lessen the proportion of change in the required exposure time (duration) in response to a slight change in the space. For this reason, even if the undesired variation or dispersion in the space occurs due to the deflection of the mask or the uneven thickness of the substrate or the like, it does not lead to the undesired variation in the required exposure time. Thus, it makes it possible to attain the patterning in a uniform manner.

Furthermore, as a light source having the continuous spectrum is used in the wavelength band (region) for effectively performing the optical patterning (i.e., an effective wavelength band), it makes it possible to perform the patterning process in more effective manner as compared to a light source having single main peak in the effective wavelength band (for example, a light source having a main peak at 172 nm, such as an excimer lamp).

Yet furthermore, according to another aspect of the present invention, in illuminance of the vacuum ultra violet light in the range where the wavelength ranges from 180 nm to 200 nm may be equal to or greater than an illuminance in a range where the wavelength ranges from 160 to 200 nm.

With this configuration, by emitting light in the wavelength region that has less generation of the active oxygen with higher light intensity, it makes it possible to yet increase the accuracy in the patterning.

Yet furthermore, according to yet another aspect of the present invention, the vacuum ultra violet light may have one or more peaks in the continuous spectrum.

With this configuration, by emitting light in the wavelength region that has less generation of the active oxygen with higher light intensity, it makes it possible to yet increase the accuracy in the patterning.

Yet furthermore, according to yet another aspect of the present invention, the pattern forming substrate may be a substrate composed of an aliphatic compound polymer.

With this configuration, by using the aliphatic compound polymer as a material for the pattern forming substrate, it makes it possible to perform the surface modification of the pattern forming substrate using the photoexcitation or the oxidative decomposition reaction with the VUV light irradiation.

Yet furthermore, according to yet another aspect of the present invention, the pattern forming substrate may be a substrate composed of cyclic olefin polymer (COP) or a cyclic olefin copolymer (COC) that is a copolymer of the COP.

With this configuration, by using a cyclic polyolefin resin as a material for the pattern forming substrate, it makes it possible to decompose the bond on the VUV light irradiation surface of the pattern forming substrate, and also to oxidize the VUV light irradiation surface of the pattern forming substrate by oxygen in the processing atmosphere. Thus, it makes it possible to perform the surface modification of the pattern forming substrate.

Yet furthermore, according to yet another aspect of the present invention, the pattern forming substrate may be a substrate in which the self-assembled monolayers (SAM) on a surface of the pattern forming substrate, and the patterned object may be manufactured by irradiating the SAM on the pattern forming substrate with the vacuum ultra violet light, and removing a portion of the SAM in a patterned shape.

With this configuration, by using the substrate in which an organic monomolecular layer such as the self-assembled monolayers (SAM) or the like is formed on the surface of the pattern forming substrate, it makes it possible to perform the photoexcitation of the organic monomolecular layer, and also the oxidative decomposition and removal (ablation) reaction thereof with the VUV light irradiation. Thus, it makes it possible to perform the patterning using the surface modification of the pattern forming substrate.

Yet furthermore, according to yet another aspect of the present invention, the pattern forming substrate may be a substrate having an admolecular layer containing carbon provided on the surface of the substrate.

With this configuration, it makes it possible to perform the patterning with the VUV light irradiation even with respect to the substrate having the admolecular layer containing carbon provided on the surface of the substrate.

Yet furthermore, according to yet another aspect of the present invention, the pattern forming substrate may be a substrate having a layer made of an organic-inorganic hybrid material provided on the surface of the substrate.

With this configuration, it makes it possible to perform the patterning with the VUV light irradiation even with respect to the substrate having the layer made of the organic-inorganic hybrid material provided on the surface of the substrate.

Yet furthermore, according to one aspect of a patterned object of the present invention, there is provided a patterned object manufactured by any of the above mentioned method for manufacturing a patterned object. With this configuration, it makes it possible to obtain the patterned object that is patterned with the higher accuracy.

Yet furthermore, according to one aspect of a light irradiation apparatus, there is provided a light irradiation apparatus, comprising: a mask stage arranged apart from the pattern forming substrate and configured to hold a mask on which a prescribed pattern is formed; a vacuum ultra violet light source unit configured to irradiate the pattern forming substrate with vacuum ultra violet light via the mask; and an atmosphere controlling unit configured to set a space between the mask and the pattern forming substrate to be an atmosphere containing oxygen. The vacuum ultra violet light source unit irradiates light, as the vacuum ultra violet light, having a continuous spectrum in a range where a wavelength ranges from 180 nm to 200 nm.

With this configuration, the space between the mask and the pattern forming substrate is set to be an atmosphere containing oxygen, and the vacuum ultra violet light source unit irradiates light having a continuous spectrum in a range where the wavelength ranges from 180 nm to 200 nm. For this reason, it makes it possible to suppress the active oxygen (ozone or the like) from being generated in the space between the mask and the pattern forming substrate as compared to the case in which the short wavelength VUV light having the wavelength less than 180 nm is emitted. As a result, it makes it possible to resolve the deterioration in the patterning accuracy due to the generated active oxygen wrapping around into the non-exposure portion.

In addition, as the concentration of the active oxygen between the mask and the pattern forming substrate is lowered, it makes it possible to lessen the proportion of the undesired variation of the required exposure time in response to a slight undesired variation in the space. As a result, it makes it possible to attain the patterning with a unified manner.

Advantageous Effect of the Invention

According to a method for manufacturing a patterned object of the present invention, as the pattern forming substrate can be irradiated with vacuum ultra violet light that has less light absorption by oxygen, it makes it possible to suppress ozone from being generated when being irradiated with the vacuum ultra violet light. As a result, it makes it possible to form a pattern that accurately follows a mask pattern with higher accuracy on the pattern forming substrate.

The above mentioned and other not explicitly mentioned objects, aspects and advantages of the present invention will become apparent to a skilled person from the following detailed description when read and understood in conjunction with the appended claims and drawings.

DESCRIPTION OF EMBODIMENTS

Hereinafter, embodiments of the present invention will be described with reference to the accompanying drawings in detail.

Figure 1:
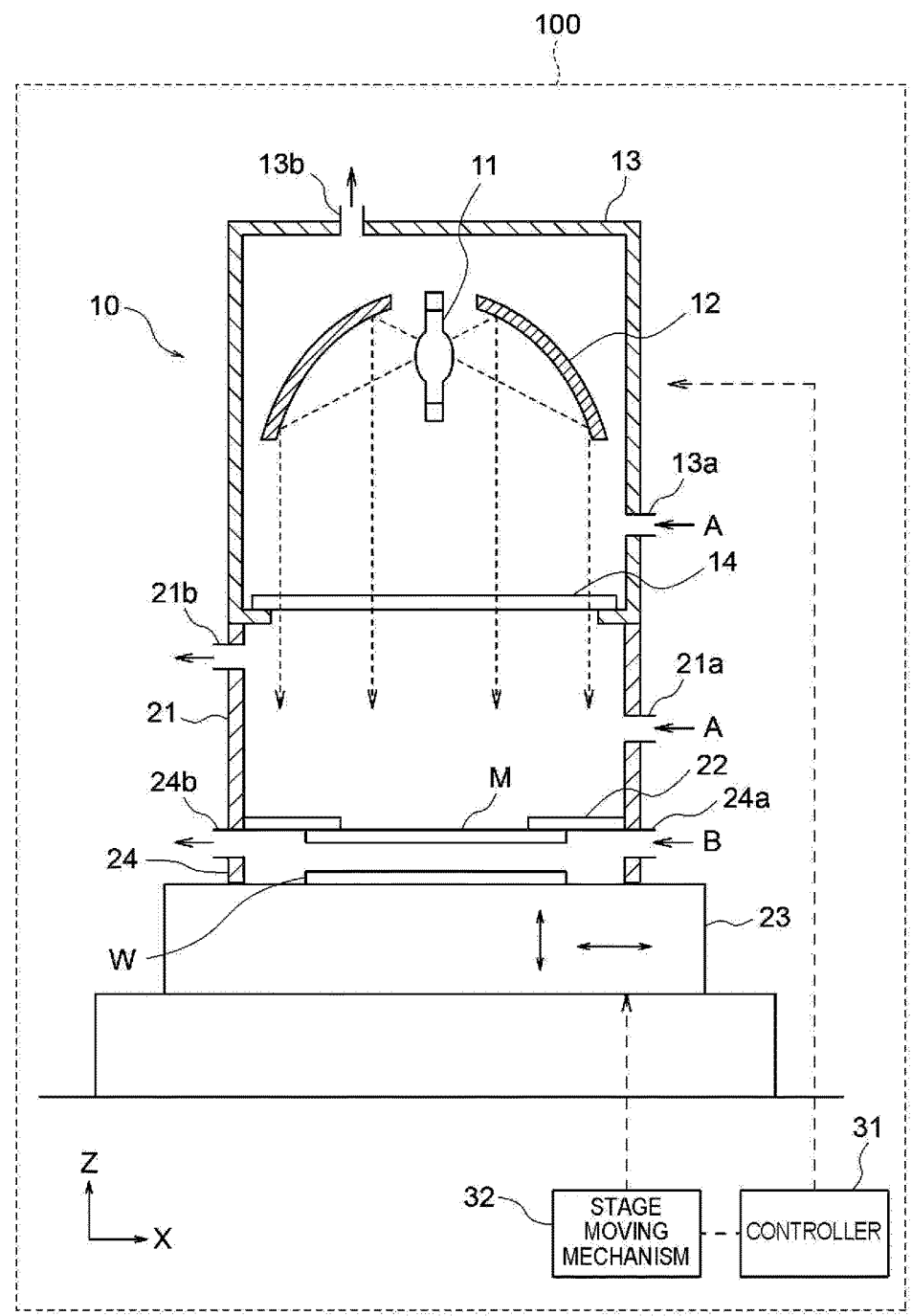
FIG. 1 is a view showing an exemplary configuration of a light irradiation apparatus according to the present embodiment.

FIG. 1 illustrates an exemplary configuration of a light irradiation apparatus according to the present embodiment.

A light irradiation apparatus 100 includes a vacuum ultra violet light source device 10 that emits vacuum ultra violet light (hereinafter referred to as "VUV light"). The vacuum ultra violet light source device 10 includes a light source 11, a paraboloid mirror 12, a lamp housing 13, and a window portion 14 provided in the lamp housing 13.

The light source 11 is a point light source and, for example, is a flash lamp having a high optical intensity in the VUV range. Here, a short arc flash lamp (hereinafter referred to as "SFL") is used as the light source 11.

Figure 2:
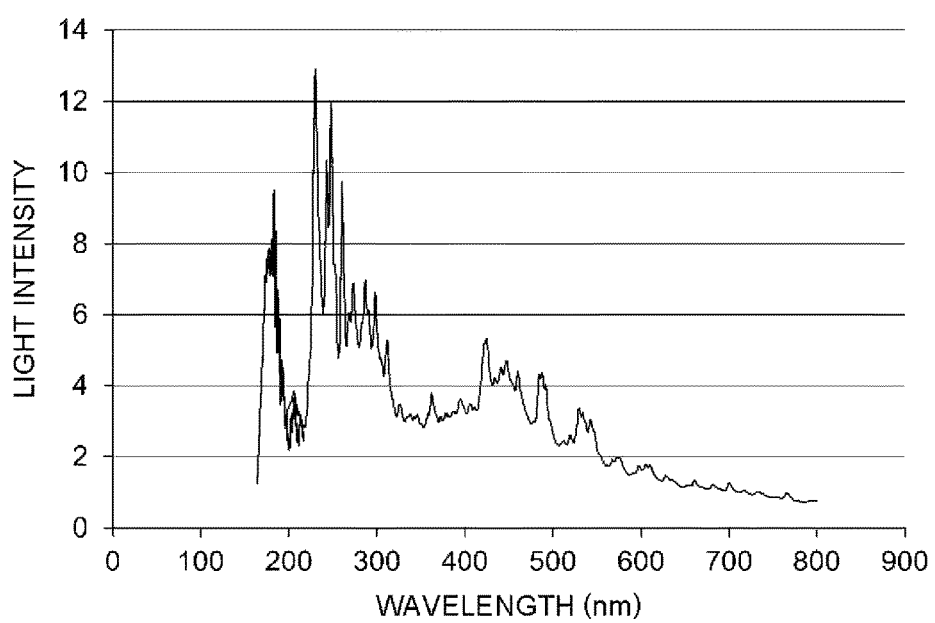
FIG. 2 is a view showing a spectral distribution of the light emitted from SFL.
Figure 3:
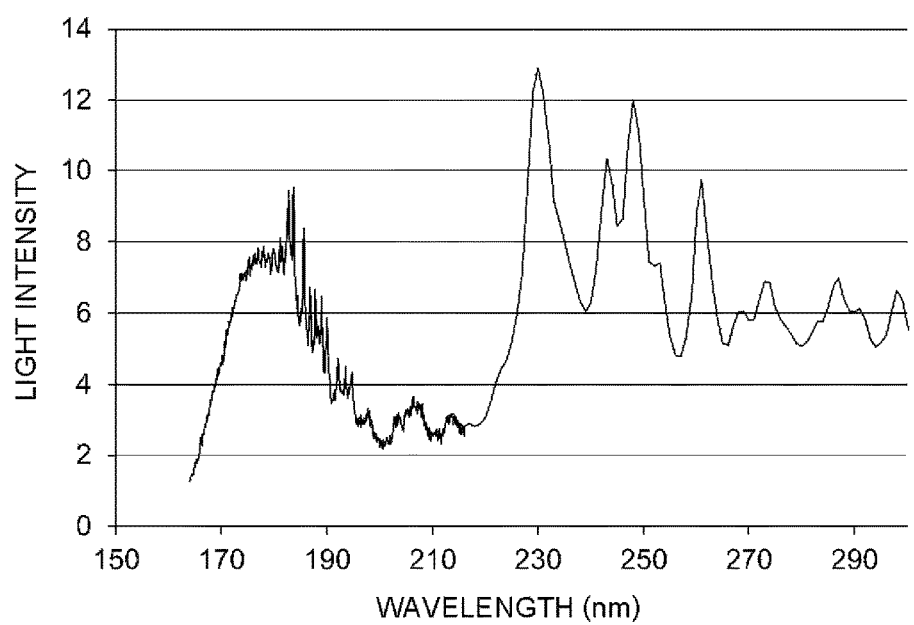
FIG. 3 is an enlarged view enlargedly showing the range between the wavelength of 150 nm and the wavelength of 300 nm shown in FIG. 2.

FIG. 2 illustrates a spectral distribution of light emitted by the SFL 11. FIG. 3 is an enlarged view of a range where the wavelength ranges from 150 nm to 300 nm in FIG. 2. It should be noted that, in FIGS. 2 and 3, the horizontal axis represents the wavelength [nm], and the vertical axis represents the optical (or light) intensity (i.e., spectral irradiance).

As illustrated in FIGS. 2 and 3, the SFL 11 emits the VUV light having a continuous spectrum in a range where the wavelength ranges from 180 nm to 200 nm. It should be noted that the continuous spectrum as used herein does not refer to a line spectrum but refers to a state in which the emission wavelength is distributed continuously across the entire range where the wavelength ranges from 180 nm to 200 nm.

As illustrated in FIG. 3, it is preferable that the SFL 11 emit the VUV light of which illuminance in a range where the wavelength ranges from 180 nm to 200 nm is equal to or greater than the illuminance in a range where the wavelength ranges from 160 nm to 180 nm. It should be noted that the illuminance (unit: $W/m^2$) as used herein refers to a radiant flux incident on a VUV light irradiation surface per unit area and is an integral of the spectral irradiance (unit: $W/m^2/nm$) in the wavelength range.

In order to set the illuminance in the range where the wavelength ranges from 180 nm to 200 nm to be equal to or greater than the illuminance in the range where the wavelength ranges from 160 nm to 180 nm, for example, the irradiation wavelength may be adjusted as appropriate through a combined use of various band-pass filters or the like.

Furthermore, as illustrated in FIG. 3, it is preferable that the SFL 11 emit the VUV light having one or more peaks in a continuous spectrum in the range where the wavelength ranges from 180 nm to 200 nm. It should be noted that the peak as used herein refers to a condition in which the spectral irradiance at a center wavelength is higher by no less than 10% than the spectral irradiance at each of the wavelengths across the center wavelength that are apart therefrom by 0.5 nm.

Figure 4:
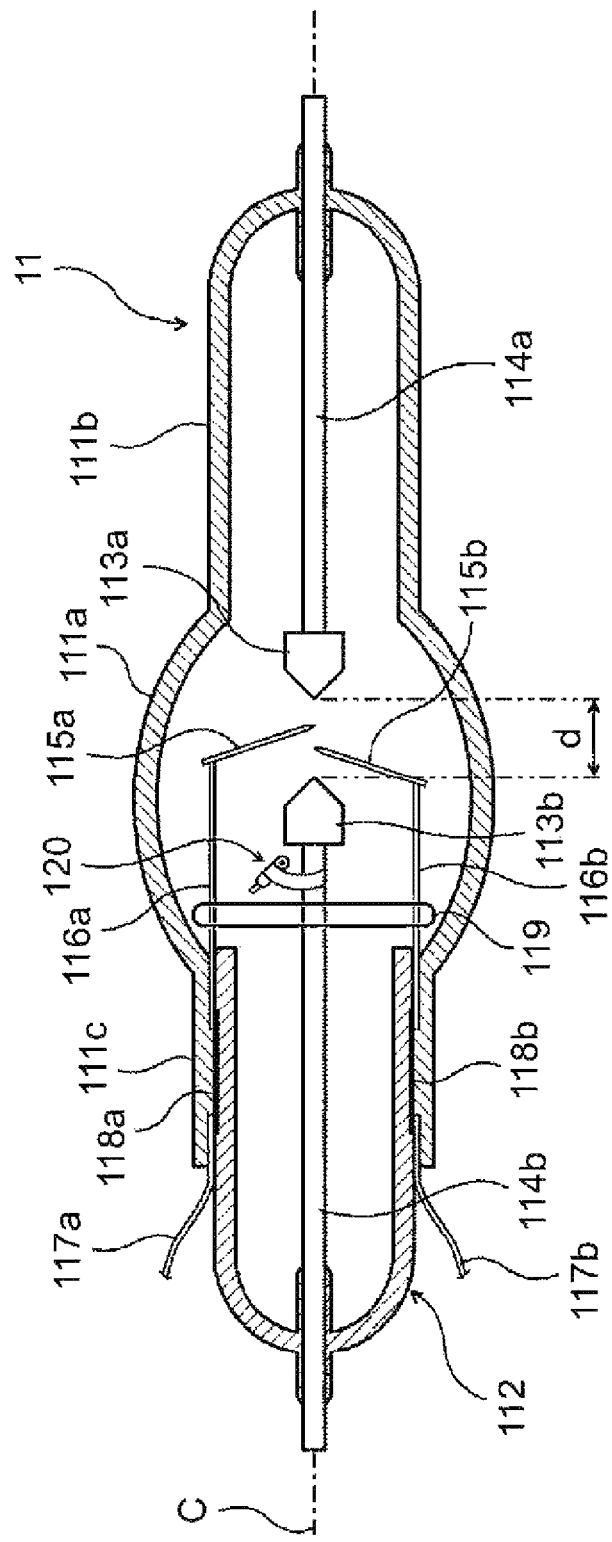
FIG. 4 is a view showing an exemplary configuration of the SFL.

A specific configuration of the SFL 11 will now be described in detail. FIG. 4 illustrates an exemplary configuration of the SFL 11.

The SFL 11 includes an arc tube 111a having an elliptical sphere shape that is made of a vacuum ultra violet light transmissive material, such as quartz glass or the like. A first sealing tube 111b and a second sealing tube 111c are continuously provided at respective ends of the arc tube 111a. Also, a sealing glass tube 112 is inserted in the second sealing tube 111c, and the second sealing tube 111c and the sealing glass tube 112 are welded at a double-tube portion. The arc tube 111a is filled, for example, with an unmixed rare gas, such as xenon (Xe) or krypton (Kr), or alternatively with a mixed gas of a small amount of $H_2$ gas or $N_2$ gas and a rare gas.

A pair of electrodes (that is, a first main electrode (anode) 113a and a second main electrode (cathode) 113b), which oppose each other, is disposed inside the arc tube 111a. The interelectrode distance d between the pair of electrodes 113a and 113b is, for example, from 1 mm to 10 mm.

An electrode rod 114a that extends outwardly from the first main electrode 113a along a tube axis C is guided to the outside through an end portion of the first sealing tube 111b. This electrode rod 114a is sealed (rod seal) by means such as a graded glass at the end portion of the first sealing tube 111b. Likewise, an electrode rod 114b that extends outwardly from the second main electrode 113b along the tube axis C is guided to the outside through an end portion of the sealing glass tube 112. This electrode rod 114b is sealed (rod seal) by means such as a graded glass at the end portion of the sealing glass tube 112.

The pair of electrodes 113a, 113b is constituted, for example, by a sintered tungsten body impregnated with a photoelectron radiating substance, such as barium oxide (BaO), calcium oxide (CaO), or alumina ($Al_2O_3$) or the like. The electrode rods 114a, 114b are constituted, for example, by tungsten.

A pair of trigger electrodes 115a and 115b, which serve as starting auxiliary electrodes, is arranged between the electrodes 113a and 113b inside the arc tube 111a. The trigger electrodes 115a, 115b are each formed to have a thin linear shape, for example, and are disposed such that their leading end portions are located with a space provided therebetween on a center line connecting the leading end of the electrode 113a and the leading end of the electrode 113b.

Furthermore, the trigger electrodes 115a, 115b are disposed at an angle to the tube axis C such that the trigger electrodes 115a, 115b come closer to the anode 113a toward their leading ends. The distance by which the leading end of one of the trigger electrodes 115a is spaced apart from the leading end of the anode 113a and the distance by which the leading end of the other trigger electrode 115b is spaced apart from the leading end of the cathode 113b are each, for example, from 0.5 mm to 1.5 mm when the interelectrode distance d between the anode 113a and the cathode 113b is 3.0 mm.

The trigger electrodes 115a, 115b are constituted, for example, by nickel, tungsten, or an alloy containing nickel or tungsten.

The trigger electrode 115a is connected to one end of a rod shaped inner lead (inner lead rod) 116a. The inner lead 116a extends in parallel to the electrode stick 114b outwardly in the direction of the tube axis and is electrically connected to an outer lead 117a via a metal foil 118a at the double-tube portion of the second sealing tube 111c and the sealing glass tube 112. Thus, a foil seal structure is formed. In a similar manner, the trigger electrode 115b is connected to one end of a rod shaped inner lead (inner lead rod) 116b. The inner lead 116b extends in parallel to the electrode stick 114b outwardly in the direction of the tube axis and is electrically connected to an outer lead 117b via a metal foil 118b in the double-tube portion of the second sealing tube 111c and the sealing glass tube 112 at a position different in a circumferential direction from the position of the metal foil 118a, for example, at a position that opposes the metal foil 118a across the tube axis C.

The pair of inner leads 116a and 116b is constituted, for example, by tungsten. Furthermore, a sparker electrode 120, which serves as a starting auxiliary electrode, for producing a discharge stably is arranged in the arc tube 111a.

The sparker electrode 120 includes, for example, a columnar (or cylindrical) head portion made of alumina ($Al_2O_3$), and a shaft portion that is continuous with the head portion. One end of a metal foil made, for example, of nickel connected to the head portion is connected to an outer peripheral surface of the electrode rod 114b, and an inner lead wire (not illustrated) made, for example, of tungsten is connected to the shaft portion. The inner lead wire is electrically connected to an outer lead wire (not illustrated) via an airtightly embedded metal foil at the double-tube portion of the second sealing tube 111c and the sealing glass tube 112 in a state in which the inner lead wire is electrically insulated from the above mentioned metal foils 118a, 118b.

Also, the pair of inner leads 116a and 116b, the electrode rod 114b, and the inner lead wire (not illustrated) for the sparker electrode 120 are provided with a common supporter member 119, and this supporter member 119 disposes the cathode 113b, the trigger electrodes 115a and 115b, and the sparker electrode 120 at appropriate positions, respectively.

The electrode rods 114a and 114b, the outer leads 117a and 117b for the trigger electrodes 115a, 115b, and the outer lead wire (not illustrated) for the sparker electrode 120 are connected to an external feeder (power supply) unit (not illustrated), respectively. This feeder unit includes a capacitor that stores predetermined energy. The feeder unit charges the capacitor to apply a high voltage across the pair of electrodes 113a and 113b and to apply a pulsed voltage to the sparker electrode 120, the trigger electrodes 115a and 115b, and the anode 113a.

Subsequently, the sparker electrode 120 first undergoes a preliminary discharge, and ultra violet light is emitted. This ultra violet light causes the cathode 113b, the anode 113a, and the trigger electrodes 115a and 115b to emit photoelectrons, and then xenon gas, for example, in the arc tube 111a is ionized. Thereafter, a preliminary discharge path is formed between the cathode 113b and the anode 113a, electrons are emitted from the cathode 113b toward the anode 113a, and an arc discharge (that is, main discharge) occurs between the cathode 113b and the anode 113a. As a result, the SFL 11 lights up, and vacuum ultra violet light is emitted.

This vacuum ultra violet light has a continuous spectrum in a range where the wavelength ranges from 180 nm to 200 nm and has a feature that its illuminance in a range where the wavelength ranges from 180 nm to 200 nm is equal to or greater than the illuminance in a range where the wavelength ranges from 160 nm to 180 nm. Furthermore, this vacuum ultra violet light has one or more peaks in a continuous spectrum in the range where the wavelength ranges from 180 nm to 200 nm.

Referring back to FIG. 1, the VUV light emitted by the SFL 11 is reflected and collimated by the paraboloid mirror 12 and exits through the window portion 14 provided in the lamp housing 13. The window portion 14 is formed, for example, by synthetic quartz having high transmittance to the VUV light. It should be noted that, alternatively, the window portion 14 may also be formed, for example, by sapphire glass, calcium fluoride, magnesium fluoride, or the like having higher transmittance to short wavelength radiation than quartz.

The window portion 14 is assembled airtightly with the lamp housing 13. An inert gas A, such as nitrogen ($N_2$) gas, is introduced into the lamp housing 13 through a gas introduction port 13a provided in the lamp housing 13, and oxygen is replaced and discharged as the interior of the lamp housing 13 is purged with an inert gas. This is done because the VUV light is highly susceptible to attenuation by absorption by oxygen, and purging the interior of the lamp housing 13 with an inert gas, such as nitrogen ($N_2$), neon (Ne), argon (Ar), or krypton (Kr), makes it possible to prevent the VUV light from being attenuated by absorption by oxygen. Also, the inert gas A that has been introduced into the lamp housing 13 cools the flash lamp 11, the paraboloid mirror 12, and so on and is then discharged through a discharge port 13b provided in the lamp housing 13.

It should be noted that the interior of the lamp housing 13 may, for example, be a vacuum or may be an atmosphere that slightly contains oxygen.

The VUV light emitted by the vacuum ultraviolet radiation source device 10 is incident on a mask M, and a workpiece (that is, pattern forming substrate) W is irradiated with the VUV light via the mask M. The mask M is obtained, for example, by depositing a light shielding (shading) material, such as chromium, on a light transmissive substrate of glass or the like, and after then carrying out etching to form a pattern (irradiation pattern) that includes a light shielding portion and a light transmissive portion in which the light shielding portion is not provided.

For example, a photomask, such as a binary mask or a phase shifted mask, can be used as the mask M. In addition, a metal mask in which aperture portions, serving as light transmissive portions, are provided in a pattern in a light shielding substrate of metal or the like can also be used as the mask M.

An enclosing member 21 that encloses an optical path through which light emitted by the vacuum ultra violet light source device 10 and to be incident on the mask M travels is provided at a light exit side of the vacuum ultraviolet radiation source device 10. The mask M is sucked and held in a horizontal state by a mask stage 22 coupled to the enclosing member 21.

The inner space defined by the window portion 14 of the vacuum ultra violet light source device 10, the enclosing member 21, the mask stage 22, and the mask M is a closed space. A gas introduction port 21a is provided in the enclosing member 21. An inert gas A, such as nitrogen ($N_2$), neon (Ne), argon (Ar), or krypton (Kr), is introduced into the closed space within the enclosing member 21 through the gas introduction port 21a, and oxygen is replaced and discharged as the interior of the enclosing member 21 is purged with an inert gas. This is done for the same reason as why oxygen inside the lamp housing 13 is purged with an inert gas. The inert gas A that has been introduced into the enclosing member 21 is discharged through a discharge port 21b provided in the enclosing member 21.

It suffices that the interior of the enclosing member 21 be at a reduced oxygen atmosphere, and the interior may be a vacuum, for example.

The workpiece W is placed on a work stage 23 and is sucked and held to the work stage 23 by, for example, a vacuum chuck mechanism. The work stage 23 is configured to be movable in XYZθ directions (the lateral direction, the depthwise direction, and the longitudinal direction of FIG. 1, and the direction of rotation about the Z axis) by a stage moving mechanism 32. The stage moving mechanism 32 is driven and controlled by a control unit 31.

The atmosphere of the space between the mask M and the workpiece W is set to the atmosphere of the air (oxygen at approximately 20 kPa) by the control unit (atmosphere control unit) 31.

Specifically, an enclosing member 24 that encloses an optical path through which the light that has passed through the mask M and with which the workpiece W is to be irradiated travels is provided at a light exit side of the mask M, and the air B is introduced into the space between the workpiece W and the mask M through an air introduction port 24a formed in the enclosing member 24. The air B that has been introduced through the air introduction port 24a is discharged through a discharge port 24b.

The atmosphere of the space between the mask M and the workpiece W is not limited to the atmosphere of the air, and any atmosphere that contains oxygen suffices.

A substrate that contains an organic component can be used as the workpiece W. For example, an aliphatic compound polymer can be used as a material for the substrate. Specific examples of the material for the substrate include, for example, a cyclic polyolefin having an alicyclic hydrocarbon group.

As a raw material for the cyclic polyolefin, dicyclopentadiene (DCPD) or a derivative of DCPD (norbornene derivative), for example, is used. As for a polymer, it is difficult to homopolymerize these cyclic olefins due to an influence of steric hindrance, and thus a method in which additive polymerization with an α-olefin is carried out or a method in which ring-opening polymerization of a cyclic olefin is carried out is used. The former polymer is referred to as a cyclic olefin copolymer (COC), and the latter polymer is referred to as a cyclic olefin polymer (COP).

The molecular structure of COC is expressed by the following formula (1), for example.

[Chem. 1]

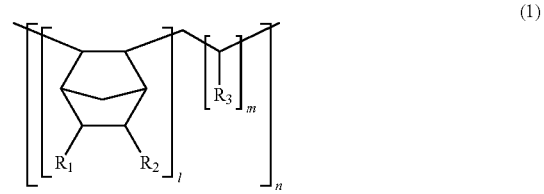

(1)

COC can be obtained, for example, by subjecting norbornene and an α-olefin having a carbon number of 2-30 to additive copolymerization with a metallocene catalyst. As an example, COC that constitutes the pattern forming substrate (that is, workpiece W) of the present embodiment is obtained by copolymerizing at least one polycyclic olefin expressed by the following formula (2)

[Chem. 2]

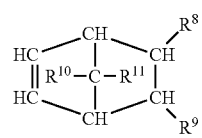

(2)

[in the formula, $R^8$, $R^9$, $R^{10}$, and $R^{11}$ are the same or different and are each a hydrogen atom or preferably a hydrocarbon group having 1 to 20 carbon atoms (e.g., $C_6$ to $C_{10}$ aryl, $C_1$ to $C_8$ alkyl, or the like)]
with at least one acyclic olefin expressed by the following formula (3)

[Chem. 3]

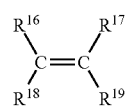

(3)

[in the formula, $R^{16}$, $R^{17}$, $R^{18}$, and $R^{19}$ are the same or different and are each a hydrogen atom or preferably a hydrocarbon group having 1 to 20 carbon atoms (e.g., $C_6$ to $C_{10}$ aryl, $C_1$ to $C_8$ alkyl, or the like)]
under the presence of a metallocene catalyst.

Representative examples of the polycyclic olefin are norbornene and tetracyclododecene, and these may be substituted by $C_1$ to $C_6$ alkyl. It is preferable that these polycyclic olefins be copolymerized with ethylene. More preferably, COC is a polymer in which norbornene and ethylene are copolymerized.

As COP, for example, a polymer obtained by subjecting a cyclic olefin monomer to ring-opening polymerization using a metathesis polymerization catalyst composed of a transition metal halide and an organometallic compound can be used.

Specific examples of the monomer of COP to be used for the pattern forming substrate (workpiece W) of the present embodiment include norbornene, an alkyl-, alkylidene-, or aromatic substituted derivative thereof, and a substituted product of a substituted or unsubstituted norbornene based monomer having as the substituent a polar group such as halogen, an ester group, an alkoxy group, a cyano group, an amide group, an imide group, or a silyl group or the like—for example, 2-norbornene, 5-methyl-2-norbornene, 5,5-dimethyl-2-norbornene, 5-ethyl-2-norbornene, 5-butyl-2-norbornene, 5-ethylidene-2-norbornene, 5-methoxycarbonyl-2-norbornene, 5-cyano-2-norbornene, 5-methyl-5-methoxycarbonyl-2-norbornene, 5-phenyl-2-norbornene, 5,6-diethoxycarbonyl-2-norbornene, 1,4-methano-1,4,4a,9a-tetrahydro-9H-fluorene, or the like; a monomer in which one or more cyclopentadiene is added to norbornene, or a derivative or substituted product thereof similar to the above—for example, 1,4:5,8-dimethano-1,4,4a,5,6,7,8,8a-octahydro naphthalene, 6-methyl-1,4:5,8-dimethano-1,4,4a,5,6,7,8,8a-octahydro naphthalene, 6-ethyl-1,4:5,8-dimethano-1,4,4a,5,6,7,8,8a-octahydro naphthalene, 6-ethylidene-1,4:5,8-dimethano-1,4,4a,5,6,7,8,8a-octahydro naphthalene, 6,6-dimethyl-1,4:5,8-dimethano-1,4,4a,5,6,7,8,8a-octahydro naphthalene, 6-methyl-6-methoxy carbonyl-1,4:5,8-dimethano-1,4,4a,5,6,7,8,8a-octahydro naphthalene, 4,9:5,8-dimethano-2,3,3a,4,4a,5,8,8a,9,9a-decahydro-1H-benzoindene, or the like; a monomer of a polycyclic structure that is a multimer of cyclopentadiene or a derivative or substituted product thereof similar to the above—for example, dicyclopentadiene, 2,3-dihydrodicyclopentadiene, 4,9:5,8-dimethano-3a,4,4a,5,8,8a,9,9a-octahydro-1H-benzoindene, or the like; an added product of cyclopentadiene and tetrahydroindene or the like, or a derivative or substituted product thereof similar to the above—for example, 1,4-methano-1,4,4a,4b,5,8,8a,9a-octahydro-9H-fluorene, 5,8-methano-3a,4,4a,5,8,8a,9,9a-octahydro-1H-benzoindene, 1,4:5,8-dimethano-1,2,3,4,4a,4b,7,8,8a,9a-decahydro-9H-fluorene, 1,4-methano-1,4,4a,9a-tetrahydrofluorene, or the like; other cyclic olefins or a derivative or substituted product thereof similar to the above—for example, cyclobutene, cyclopentene, cyclohexene, cyclooctene, 5,6-dihydrocyclopentadiene, 3a,4,7,7a-tetrahydroindene, 4-ethylcyclohexene, etc.; and the like. These monomers may be used alone, or two or more of these monomers may be used in combination.

The pattern forming substrate (workpiece W) is not limited to a substrate composed of COC or COP, and, for example, a substrate of any synthetic resin, such as acryl, PE (polyethylene), or PP (polypropylene), can also be employed. For example, for the pattern forming substrate (workpiece W), a synthetic resin substrate of polystyrene (PS), acrylonitrile styrene (AS), acrylonitrile butadiene styrene (ABS), polyethylene terephthalate (PET), polycarbonate (PC), polysulfone (PSF), polyether sulfone (PES), polyphenylene sulfide (PPS), polyamide imide (PAI), polyimide (PI), polyether ether ketone (PEEK), a liquid crystal polymer (LCP), parylene, a phenolic resin, or an epoxy resin or the like can also be employed. In addition, for the pattern forming substrate (workpiece W), a synthetic resin substrate of polyvinyl alcohol (PVA), ethylene vinyl alcohol (EVOH), polymethyl methacrylate (PMMA), polyamide (PA), or a urethane resin can also be employed. The material for the pattern forming substrate (workpiece W) is not limited to a synthetic resin having a C—H bond, and a fluoroplastic having a C—F bond, such as polytetrafluoroethylene, can also be employed.

Furthermore, for the pattern forming substrate (workpiece W), a substrate made of a photoresist material, such as a bisazido compound, a novolac resin (one type of phenol), naphthoquinone diazide (NQD), polyhydroxystyrene (PHS), or a photoacid generator (PAG), may also be employed. In addition, for the pattern forming substrate (workpiece W), a substrate made of an organic electronics material, such as pentacene, rubrene, BTBT, DNTT, P3HT, or PEDOT:PSS, may also be employed.

The pattern forming substrate (workpiece W) is selected as appropriate in accordance with an intended use of the patterned object.

As the pattern forming substrate (workpiece W), a substrate in which an organic monolayer (e.g., self-assembled monolayer (SAM)) is provided on a base material made of an appropriate material can also be used.

The base material on which the organic monolayer is to be formed is not particularly limited and is select as appropriate with the intended use of the patterned object, the type of molecules constituting the organic monolayer, or the like taken into consideration. Specifically, the organic monolayer can be provided on a variety of base materials made of metal, such as gold, silver, copper, platinum, or iron or the like, an oxide, such as quartz glass or an aluminum oxide or the like, a compound semiconductor, such as GaAs or InP or the like, a high-polymer material, or the like.

For the material that constitutes the organic monolayer, any organic molecules that can be excited by the VUV light and decomposed can be employed. When the organic monolayer is a SAM, an organic molecule that has a functional group which chemically reacts with the surface of the base material and that is self-assembled through an intermolecular interaction may be used.

Specifically, as an organic molecule that constitutes the SAM, a phosphonic acid compound expressed by the following general formula (4) can be used.

[Chem. 4]

(4)

In the above formula (4), $R^1$ is a substituted or unsubstituted aliphatic hydrocarbon group or aromatic hydrocarbon group that may contain a halogen atom or a heteroatom, and is preferably a substituted or unsubstituted and straight-chain or branched-chain alkyl group, a substituted or unsubstituted benzyl group, or a substituted or unsubstituted phenoxy group.

Specific examples of such phosphonic acid compounds include butylphosphonic acid, hexylphosphonic acid, octylphosphonic acid, decylphosphonic acid, tetradecylphosphonic acid, hexadecylphosphonic acid, octadecylphosphonic acid, 6-phosphonohexanoic acid, 11-acetylmercaptoundecylphosphonic acid, 11-hydroxyundecylphosphonic acid, 11-mercaptoundecylphosphonic acid, 1H,1H,2H,2H-perfluorooctanephosphonic acid, 11-phosphonoundecylphosphonic acid, 16-phosphonohexadecanoic acid, 1,8-octanediphosphonic acid, 1,10-decyldiphosphonic acid, 1,12-dodecyldiphosphonic acid, benzylphosphonic acid, 4-fluorobenzylphosphonic acid, 2,3,4,5,6-pentafluorobenzylphosphonic acid, 4-nitrobenzylphosphonic acid, 12-pentafluorophenoxydodecylphosphonic acid, (12-phosphonododecyl)phosphonic acid, 16-phosphonohexadecanoic acid, 11-phosphonoundecanoic acid, difluorobenzylphosphonic acid, methoxybenzylphosphonic acid, aminobenzylphosphonic acid, phenylphosphonic acid, and the like. Aside from the compound of the formula (1), a compound such as [2-[2-(2-methoxyethoxy)ethoxy]ethyl]phosphonic acid can also be employed.

As another example of the organic molecule that constitutes the SAM, a thiol compound expressed by the following general formula (5) can also be used.

[Chem. 5]

$$R^2\text{—SH} \qquad (5)$$

In the above formula (5), $R^2$ is a substituted or unsubstituted aliphatic hydrocarbon group or aromatic hydrocarbon group that may contain a halogen atom or a heteroatom. A derivative of the compound of the above formula (5) in which the thiol group is further substituted can also be employed.

Specific examples of such thiol compounds and derivatives thereof may include 1-butanethiol, 1-decanethiol, 1-dodecanethiol, 1-heptanethiol, 1-hexadecanethiol, 1-hexanethiol, 1-nonanethiol, 1-octadecanethiol, 1-octanethiol, 1-pentadecanethiol, 1-pentanethiol, 1-propanethiol, 1-tetradecanethiol, 1-undecanethiol, 11-mercaptoundecyl trifluoroacetate, 1H,1H,2H,2H-perfluorodecanethiol, 2-butanethiol, 2-ethylhexanethiol, 2-methyl-1-propanethiol, 2-methyl-2-propanethiol, 3,3,4,4,5,5,6,6,6-nonafluoro-1-hexanethiol, 3-mercapto-N-nonylpropionamide, 3-methyl-1-butanethiol, 4-cyano-1-butanethiol, butyl 3-mercaptopropionate, cis-9-octadecene-1-thiol, methyl 3-mercaptopropionate, tert-dodecylmercaptan, tert-nonylmercaptan, 1,11-undecanedithiol, 1,16-hexadecanedithiol, 1,2-ethanedithiol, 1,3-propanedithiol, 1,4-butanedithiol, 1,5-pentanedithiol, 1,6-hexanedithiol, 1,8-octanedithiol, 1,9-nonanedithiol, 2,2'-(ethylenedioxy)diethanethiol, 2,3-butanedithiol, 5,5'-bis(mercaptomethyl)-2,2'-bipyridine, hexa(ethylene glycol)dithiol, tetra(ethylene glycol)dithiol, benzene-1,4-dithiol, (11-mercaptoundecyl)-N,N,N-trimethyl ammonium bromide, (11-mercaptoundecyl)hexa(ethylene glycol), (11-mercaptoundecyl)tetra(ethylene glycol), 1(11-mercaptoundecyl)imidazole, 1-mercapto-2-propanol, 11-(1H-pyrrole-1-yl)undecane-1-thiol, 11-(ferrocenyl)undecanethiol, 11-amino-1-undecanethiol hydrochloride, 11-azido-1-undecanethiol, 11-mercapto-1-undecanol, 11-mercaptoundecaneamide, 11-mercaptoundecanoic acid, 11-mercaptoundecylhydroquinone, 11-mercaptoundecylphosphonic acid, 11-mercaptoundecylphosphoric acid, 12-mercaptododecanoic acid, 12-mercaptododecanoic acid NHS ester, 16-mercaptohexadecanoic acid, 3-amino-1-propanethiol hydrochloride, 3-chloro-1-propanethiol, 3-mercapto-1-propanol, 3-mercaptopropionic acid, 4-mercapto-1-butanol, 6-(ferrocenyl)hexanethiol, 6-amino-1-hexanethiol hydrochloride, 6-mercapto-1-hexanol, 6-mercaptohexanoic acid, 8-mercapto-1-octanol, 8-mercaptooctanoic acid, 9-mercapto-1-nonanol, triethylene glycol mono-11-mercaptoundecyl ether, 1,4-butanedithiol diacetate, [11-(methylcarbonylthio)undecyl]hexa(ethylene glycol)methyl ether, [11-(methylcarbonylthio)undecyl]tetra(ethylene glycol), [11-methylcarbonylthio)undecyl]tri(ethylene glycol)acetic acid, [11-methylcarbonylthio)undecyl]tri(ethylene glycol)methyl ether, hexa(ethylene glycol)mono-11-(acetylthio)undecyl ether, 5,5'-[1,4-phenylenebis(2,1-ethanediyl-4-1-phenylene)]bis(thioacetate), S-[4-[2-[4-(2-phenylethynyl)phenyl]ethynyl]phenyl]thioacetate, S-(10-undecenyl)thioacetate, thioacetic acid S-(11-bromoundecyl), S-(4-azidobutyl)thioacetate, S-(4-bromobutyl)thioacetate (containing copper as stabilizer), thioacetic acid S-(4-cyanobutyl), 1,1',4',1"-terphenyl-4-thiol, 1,4-benzenedimethanethiol, 1-adamantanethiol, ADT, 1-naphthalenethiol, 2-phenylethanethiol, 4'-bromo-4-mercaptobiphenyl, 4'-mercaptobiphenylcarbonitrile, 4,4'-bis(mercaptomethyl)biphenyl, 4,4'-dimercaptostilbene, 4-(6-mercaptohexyloxy)benzyl alcohol, 4-mercaptobenzoic acid, 9-fluorenylmethylthiol, 9-mercaptofluorene, biphenyl-4,4-dithiol, biphenyl-4-thiol, cyclohexanethiol, cyclopentanethiol, m-carborane-1-thiol, m-carborane-9-thiol, p-terphenyl-4,4"-dithiol, thiophenol, biphenyldithiol, and the like.

Furthermore, in another example, a silane compound expressed by the following general formula (6) can be used as the SAM.

[Chem. 6]

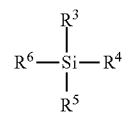

(6)

In the above formula (6), $R^3$-$R^6$ are a substituted or unsubstituted aliphatic hydrocarbon group or aromatic hydrocarbon group that may contain a halogen atom or a heteroatom.

Specific examples of such silane compounds may include bis(3-methylamino)propyl)trimethoxysilane, bis(trichlorosilyl)methane, chloromethyl(methyl)dimethoxysilane, dimethoxy(3-glycidyloxypropyl)methylsilane, dimethoxy(methyl)vinylsilane, dimethoxy(methyl)octylsilane, dimethoxymethylvinylsilane, N,N-dimethyl-4-[(trimethylsilyl)ethynyl]aniline, 3-glycidoxypropyldimethylethoxysilane, methoxy(dimethyl)octadecylsilane, methoxy(dimethyl)octylsilane, octenyltrichlorosilane, trichloro[2-(chloromethyl)allyl]silane, trichloro(dichloromethyl)silane, 3-(trichlorosilyl)propyl methacrylate, N-[3-(trimethoxysilyl)propyl]-N'-(4-vinylbenzyl)ethylenediamine hydrochloride, tridecafluorooctyltrimethoxysilane, 2-[(trimethylsilyl)ethynyl]anisole, tris[3-(trimethoxysilyl)propyl]isocyanurate, azidotrimethylsilane, 3-[2-(2-aminoethylamino)ethylamino]propyltrimethoxysilane, [3-(2-aminoethylamino)propyl]trimethoxysilane, 3-aminopropyl(diethoxy)methylsilane, (3-aminopropyl)triethoxysilane, (3-aminopropyl)trimethoxysilane, allyltriethoxysilane, allyltrichlorosilane, allyltrimethoxysilane, isobutyl(trimethoxy)silane, ethoxydimethylphenylsilane, ethoxytrimethylsilane, octamethylcyclotetrasiloxane, (3-chloropropyl)trimethoxysilane, chloromethyltriethoxysilane, chloromethyltrimethoxysilane, (3-glycidyloxypropyl)trimethoxysilane, 3-glycidoxypropyldimethoxymethylsilane, 3-cyanopropyltriethoxysilane, 3-cyanopropyltrichlorosilane, [3-(diethylamino)propyl]trimethoxysilane, diethoxydiphenylsilane, diethoxydimethylsilane, diethoxy(methyl)phenylsilane, dichlorodiphenylsilane, diphenylsilanediol, (N,N-dimethylaminopropyl)trimethoxysilane, dimethyloctadecyl[3-(trimethoxysilyl)propyl]ammonium chloride, dimethoxydiphenylsilane, dimethoxy-methyl(3,3,3-trifluoropropyl)silane, triethoxy(isobutyl)silane, triethoxy(octyl)silane, 3-(triethoxysilyl)propionitrile, 3-(triethoxysilyl)propyl isocyanate, triethoxyvinylsilane, triethoxyphenylsilane, trichloro(octadecyl)silane, trichloro(octyl)silane, trichlorocyclopentylsilane, trichloro(3,3,3-trifluoropropyl)silane, trichloro(1H,1H,2H,2H-perfluorooctyl)silane, trichlorovinylsilane, trichloro(phenyl)silane, trichloro(phenethyl)silane, trichloro(hexyl)silane, trimethoxy[2-(7-oxabicyclo[4.1.0]hepta-3-yl)ethyl]silane, trimethoxy(octadecyl)silane, trimethoxy(octyl)silane, trimethoxy(7-octene-1-yl)silane, 3-(trimethoxysilyl)propyl acrylate, N-[3-(trimethoxysilyl)propyl]aniline, N-[3-(trimethoxysilyl)propyl]ethylenediamine, 3-(trimethoxysilyl)propyl methacrylate, 1-[3-(trimethoxysilyl)propyl]urea, trimethoxy(3,3,3-trifluoropropyl)silane, trimethoxy(2-phenylethyl)silane, trimethoxyphenylsilane, trimethoxy[3-(methylamino)propyl]silane, p-tolyltrichlorosilane, dodecyltriethoxysilane, 1H,1H,2H,2H-perfluorooctyltriethoxysilane, 1H,1H,2H,2H-perfluorodecyltriethoxysilane, 1H,1H,2H,2H-perfluorododecyltrichlorosilane, 1,2-bis(triethoxysilyl)ethane, 1,2-bis(trichlorosilyl)ethane, 1,6-bis(trichlorosilyl)hexane, 1,2-bis(trimethoxysilyl)ethane, bis[3-(trimethoxysilyl)propyl]amine, 3-[bis(2-hydroxyethyl)amino]propyl-triethoxysilane, vinyltrimethoxysilane, butyltrichlorosilane, tert-butyltrichlorosilane, (3-bromopropyl)trichlorosilane, (3-bromopropyl)trimethoxysilane, n-propyltriethoxysilane, hexachlorodisilane, hexadecyltrimethoxysilane, methoxytrimethylsilane, (3-mercaptopropyl)trimethoxysilane, (3-iodopropyl)trimethoxysilane, trichlorophenylsilane, and the like.

These foregoing organic molecules that constitute the SAM are merely examples and are not limited thereto.

As the pattern forming substrate (workpiece W), a substrate in which an admolecular layer containing carbon is provided on the surface of a base material made of an appropriate material can also be used. It is preferable that an inorganic layer be provided as the admolecular layer. The base material on which the inorganic layer is provided is not particularly limited and is selected as appropriate with the intended use of the patterned object, the type of the inorganic layer, and the like taken into consideration. For example, for the pattern forming substrate (workpiece W), a substrate in which $CO_2$ is applied as an inorganic layer on a Si substrate having a $SiO_2$ film laminated on the surface thereof can be used. As the material that constitutes the inorganic layer containing carbon, for example, a material that consists substantially of carbon, such as carbon nanotube, carbon nanohorn, graphene, or fullerene, can also be used.

As the pattern forming substrate (workpiece W), a substrate having a layer made of an organic-inorganic hybrid material provided on the surface thereof can also be used. Examples of the organic-inorganic hybrid material include polysilicone-based (polymethylsilsesquioxane or the like) materials and carbon fiber reinforced plastics (CFRP).

The process of irradiating the workpiece W with the VUV light is carried out as follows.

First, the control unit 31 controls the driving of a vacuum chuck mechanism and so on and holds the mask M set at a predetermined position on the mask stage 22 through vacuum suction. Next, the control unit 31 lowers the work stage 23 with the stage moving mechanism 32 and places the workpiece W on the work stage 23. Thereafter, the control unit 31 raises the work stage 23 with the stage moving mechanism 32 and sets the workpiece W at a predetermined VUV light irradiation position. Next, the control unit 31 moves the work stage 23 in the XYθ directions with the stage moving mechanism 32 and aligns the mask M with the workpiece W (alignment). In other words, the control unit 31 aligns an alignment mark printed on the mark M with an alignment mark printed on the workpiece W.

Upon the alignment of the mask M and the workpiece W being finished, the vacuum ultraviolet radiation source device 10 irradiates the workpiece W with the VUV light, which is parallel light, via the mask M and carries out an optical patterning process through the surface modifying of the workpiece W. Upon the optical patterning process being finished, the control unit 31 lowers the work stage 23 with the stage moving mechanism 32, stops supplying a vacuum to the work stage 23, and produces a state in which the irradiated workpiece W can be removed from the work stage 23.

As described above, in the light irradiation apparatus 100 of the present embodiment, the mask M in which a pattern is formed is prepared, the mask M and the workpiece W are disposed proximal to and in parallel to each other, and only a portion of the surface of the workpiece W of which the characteristics are to be changed is irradiated with the parallel VUV light via the mask M. In this manner, a pattern including a modified portion and a non-modified portion is formed in the surface of the workpiece W.

At this point, the light irradiation apparatus 100 sets the space between the mask M and the workpiece W to an atmosphere containing oxygen, such as the air, and irradiates the workpiece W with the VUV light in the above mentioned atmosphere. The vacuum ultraviolet radiation source device 10 emits, as the VUV light with which the workpiece W is irradiated, the VUV light having a continuous spectrum in a range where the wavelength ranges from 180 nm to 200 nm.

The present inventor(s) has found that, of the wavelength range for effectively carrying out optical patterning (effective wavelength range), less optical absorption by oxygen occurs in a range where the wavelength ranges from 180 nm to 200 nm, whereas optical absorption by oxygen occurs noticeably at a shorter wavelength side in a range where the wavelength ranges from 160 nm to 180 nm or shorter. Furthermore, the present inventor(s) has found that, in order to effectively carry out the optical patterning, a light source having a continuous spectrum in the effective wavelength range is preferable to a light source having a single main peak in the effective wavelength range, such as an excimer lamp, (having a main peak at 172 nm).

In other words, when an atmosphere containing oxygen is irradiated with the VUV light, the oxygen molecules absorb the VUV light and become excited, and thus active oxygen (ozone or singlet oxygen atom) is generated. However, by using light at a wavelength in a range from 180 nm to 200 nm as the VUV light, the amount of generated active oxygen can be reduced as compared to a case in which VUV light at a wavelength shorter than 180 nm is used.

Figure 5:
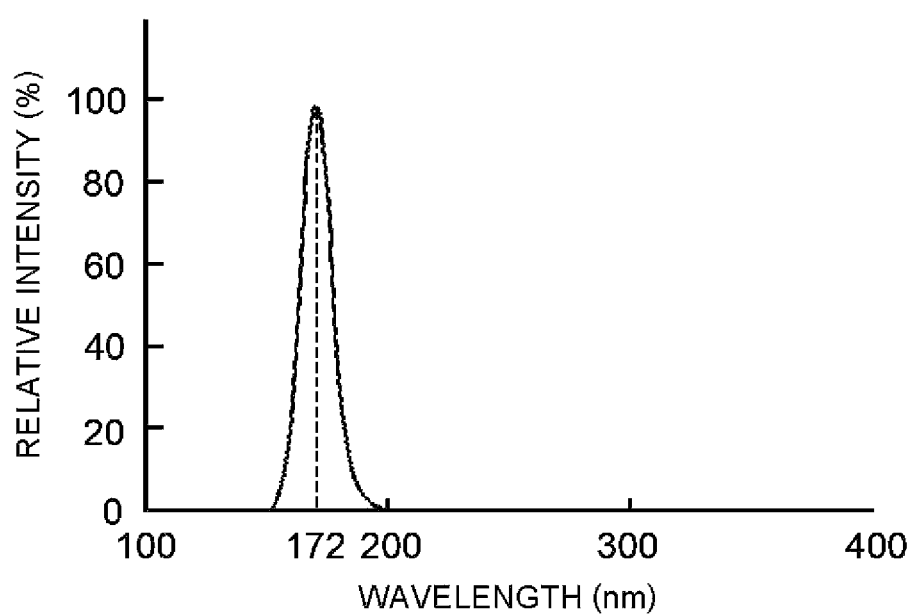
FIG. 5 is a view showing a spectral distribution of the light emitted from an excimer lamp.

When the space between a mask and a workpiece is set to an atmosphere containing oxygen and an excimer lamp that emits the VUV light having a wavelength shorter than 180 nm (e.g., 172 nm) and having a line spectrum as illustrated in FIG. 5, for example, is used as a VUV light source, a large amount of active oxygen is generated in the space between the mask and the workpiece through the VUV light irradiation. This active oxygen reacts with organic molecules of the surface of the workpiece and causes the organic molecules to decompose.

In the optical patterning process, ideally, oxidative decomposition reaction by the VUV light occurs only at the surface of the workpiece irradiated with the VUV light, and a pattern is thus formed. However, when a large amount of active oxygen is generated in the space between the mask M and the workpiece W at the time of the VUV light irradiation as described above, this active oxygen flows into the portion (non-exposure portion) of the surface of the workpiece W that is covered by a shading portion of the mask M. Then, oxidative decomposition reaction of the active oxygen with the non-exposure portion of the surface of the workpiece W occurs, and the organic molecules in the non-exposure portion partially decompose, and the pattern accuracy is thus reduced.

In contrast, in the present embodiment, as described above, in the optical patterning process in an atmosphere containing oxygen, the VUV light irradiation having a continuous spectrum in a range where the wavelength ranges from 180 nm to 200 nm is used. Therefore, optical absorption by oxygen at the time of VUV light irradiation can be reduced in the space between the mask M and the workpiece W, and generation of a large amount of active oxygen in the stated space can be suppressed.

Thus, active oxygen flowing into the non-exposure portion can be reduced.

In this manner, by adjusting the wavelength of the VUV light, an amount of active oxygen (ozone) generated at the time of the VUV light irradiation can be adjusted. Therefore, a decrease in the accuracy in the pattern formed on the substrate caused by active oxygen (ozone) generated through the VUV light irradiation can be prevented.

Furthermore, since the VUV light having a continuous spectrum in the effective wavelength range is used, the optical patterning process can be carried out more effectively as compared to a case in which there is a single main peak in the effective wavelength range as in the VUV light emitted by an excimer lamp illustrated in FIG. 5, for example.

By using the VUV light having one or more peaks in a continuous spectrum in a range where the wavelength ranges from 180 nm to 200 nm, an optical patterning process that uses a light source with intense light emission in a wavelength range in which less active oxygen is generated becomes possible. Thus, the pattern accuracy can be further increased.

Furthermore, since a short-arc flash lamp is used as the light source, the workpiece W can be irradiated appropriately with the VUV light that satisfies the above condition.

By setting the interelectrode distance d of the short-arc flash lamp to a short distance of 1-10 mm, the size of the arc can be reduced, or in other words, a point light source can be achieved. In this manner, by using a light source that can be considered as a point light source, the field of view of the VUV light incident on the pattern forming substrate can be reduced. In other words, the optical axis of the VUV light incident on the pattern forming substrate via the mask can be made substantially normal to the mask, and light that flows into the portion (non-exposure portion) of the pattern forming substrate that is shaded with the mask can be reduced. Thus, a reduction in the pattern linewidth can be achieved.

Furthermore, even in a case in which the mask M and the workpiece W are disposed proximal to each other, the concentration of the active oxygen filling the space between the mask M and the workpiece W is reduced. Thus, the required exposure time is not affected by a slight change in the aforementioned space, and the required exposure time can be set with ease. Since it becomes possible to dispose the mask M and the workpiece W proximal to each other, the pattern accuracy can be further improved.

In addition, since VUV light having a wavelength at which optical absorption by oxygen is small is used as the VUV light used in the optical patterning, it is not necessary to purge the entire VUV light irradiation atmosphere with an inert gas. Therefore, the cost can be reduced.

As the workpiece W, an organic substrate made of COP, COC, or the like, for example, can be used. As the organic substrate itself is irradiated with the VUV light, oxidative decomposition reaction is induced at the surface of the substrate, and the surface modifying effect can be obtained. At this point, a polar functional group (hydrophilic functional group) can be formed on the surface of the substrate through the VUV light irradiation, and a variety of surface modifications become possible. This technique can be used, for example, in functionalization of a microchip substrate.

As the workpiece W, a substrate having a SAM formed on the surface thereof can also be used. As the SAM is irradiated with the VUV light, oxidative decomposition removal reaction of the SAM is induced, and the optical patterning of the SAM becomes possible. The patterned SAM can be used, for example, as a gate insulating film for an organic thin-film transistor. It is also possible to form a fine functional pattern by forming a hydrophilic-hydrophobic pattern by irradiating a hydrophobic SAM with the VUV light and by applying a functional ink on the hydrophilic-hydrophobic pattern.

EXAMPLE 1

Hereinafter, effects of the present invention will be described through examples.

First, pattern forming substrates were fabricated by using, as materials for the respective substrates, COC obtained by copolymerizing a norbornene derivative and an α-olefin, such as ethylene, with a metallocene catalyst and COP obtained by subjecting a norbornene derivative with the use of a metallocene polymerization catalyst. Next, the pattern forming substrates were irradiated with vacuum ultra violet light by using, as respective light sources, a short-arc flash lamp (SFL) illustrated in FIG. 4 and an excimer lamp, and patterning was carried out. Thereafter, the accuracy of the obtained patterns was evaluated.

As the SFL, one in which the interelectrode distance is 3 mm and the arc tube is filled with xenon gas (Xe) at a filling pressure of 5 atm was used. This SFL was powered at 10 Hz by charged energy (3.6 J) of a capacitor having a capacitance of 20 μF charged at 600 V.

As the excimer lamp, a double-pipe excimer lamp in which the arc tube is filled with xenon gas (Xe) at a filling pressure of 0.5 atm was used. The arc tube having a diameter of 20 mm and a length of 80 mm in the direction of the tube axis was used. The excimer lamp was powered at 100 W.
(Patterning Method)

The pattern forming substrates were disposed directly underneath the centers of the respective lamps at a distance of 40 mm and were exposed via a mask. The mask was disposed over the pattern forming substrate with a gap of 20 μm or 5 μm provided therebetween. The space between the lamp and the mask was purged with nitrogen, and the atmosphere of the gap (the space between the mask and the pattern forming substrate) was the air (oxygen at approximately 20 kPa), and the exposure was carried out for one minute.

Thereafter, a SAM was formed through a gas-phase process, a fluorescent dye TAMRA (Tetramethylrhodamine) was modified, and the linewidth at the center portion of the exposure region of 20 μm×100 μm (the direction spanning 100 μm corresponds to the axial direction of the lamp) was measured with the use of a fluorescence microscope.

For the SAM, an aminosilane SAM (AHAPS-SAM) fabricated from n-(6-aminohexyl)aminopropyltrimethoxysilane having an amino group terminal was used, and the heating temperature at the time of forming the SAM was set to 100 degrees C.

Figure 6:
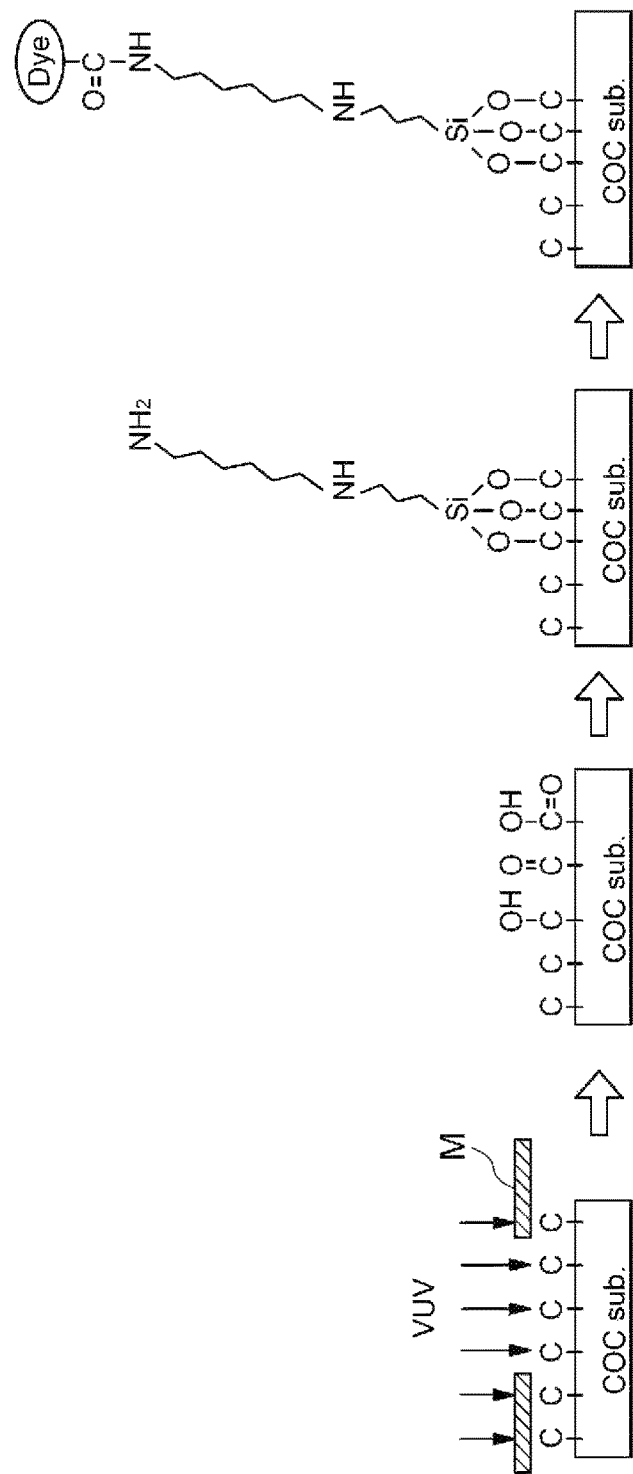
FIG. 6 is a view showing a method for evaluating a pattern of COC.

As illustrated in FIG. 6, when the surface of COC is irradiated with the VUV light via the mask M, a polar functional group is formed on the surface irradiated with the VUV light through VUV oxidation reaction. The AHAPS-SAM is formed through a reaction of a hydroxyl group on the surface of the exposed portion with an organic silane molecule, and the fluorescent dye TAMRA is bonded to an amino group at the terminal of the AHAPS-SAM. Therefore, when the substrate in which the fluorescent dye TAMRA has been modified is observed with a fluorescence microscope, the exposed portion looks brighter than the non-exposed portion. Thus, the accuracy of the pattern formed in COC can be evaluated. The same applies to COP as well.

The patterns formed in COC and COP respectively in the case in which the SFL was used as the light source and in the case in which the excimer lamp was used as the light source were measured, and the results shown in Table 1 were obtained.

TABLE 1

| | Oxygen 20 kPa | | | |
|---|---|---|---|---|
| | Gap 20 μm Linewidth [μm] | | Gap 5 μm Linewidth [μm] | |
| | SFL | Excimer | SFL | Excimer |
| COC | 21.2 | 24.5 | 20.8 | 21.9 |
| COP | 21.3 | 24.1 | 20.9 | 21.5 |

As shown in Table 1, in patterning in an atmosphere containing oxygen, when the SFL that emits the VUV light having a continuous spectrum in a range where the wavelength ranges from 180 nm to 200 nm is used as a light source, the patterns formed in COC and COP have a linewidth that is substantially equivalent to the mask size (20 μmL/S (pattern constituted by a repetition of a line and a space that are each 20 μm)). In this manner, it was confirmed that, by using the SFL having a continuous spectrum in a range where the wavelength ranges from 180 nm to 200 nm as the light source, a pattern that accurately follows the mask pattern can be obtained with high accuracy, as compared to a case in which an excimer lamp is used as the light source.

It was also confirmed that, when the SFL is used, high pattern accuracy can be obtained in either of the cases in which the gap is 20 μm and the gap is 5 μm (a change in the pattern accuracy associated with the size of the gap is small). In other words, it was confirmed that, when the SFL is used, a gap dependence (a change in the pattern accuracy associated with the gap) is small as compared to a case in which an excimer lamp is used.

In this manner, it was confirmed that, when an organic material substrate, such as COC or COP, itself is irradiated with the VUV light and patterned, favorable patterning can be achieved by irradiating the substrate with the VUV light having a continuous spectrum in a range where the wavelength ranges from 180 nm to 200 nm.

EXAMPLE 2

First, phosphonic acid-based, silane-based, and thiol-based self-assembled monolayers (SAM) were formed in a thickness of 1-3 nm on the surface of substrates, and the pattern forming substrates were fabricated. As the substrates, a substrate of aluminum oxide was used for the phosphonic acid-based SAM, a substrate of quartz glass was used for the silane-based SAM, and a gold substrate was used for the thiol-based SAM. Next, the pattern forming substrates were irradiated with vacuum ultraviolet radiation by using, as a light source, a short-arc flash lamp (SFL) illustrated in FIG. 4 and an excimer lamp, and patterning was carries out. Thereafter, the accuracy of the obtained patterns was evaluated.

As the SFL, one in which the interelectrode distance is 3 mm and the arc tube is filled with xenon gas (Xe) at a filling pressure of 5 atm was used. This SFL was powered at 10 Hz by charged energy (3.6 J) of a capacitor having a capacitance of 20 μF charged at 600 V.

As the excimer lamp, a double-pipe excimer lamp in which the arc tube is filled with xenon gas (Xe) at a filling pressure of 0.5 atm was used. The arc tube having a diameter of 20 mm and a length of 80 mm in the direction of the tube axis was used. The excimer lamp was powered at 100 W.

(Patterning Method)

The pattern forming substrates were disposed directly underneath the centers of the respective lamps at a distance of 40 mm and were exposed via a mask. The mask was disposed over the pattern forming substrate with a gap of 20 μm or 5 μm provided therebetween. The space between the lamp and the mask was purged with nitrogen, and the atmosphere of the gap (the space between the mask and the pattern forming substrate) was the air (oxygen at approximately 20 kPa). With regard to the exposure time, the surface of the pattern forming substrate was exposed via a sufficiently large mask aperture portion (10 mm×10 mm) in advance, and the exposure time was determined such that the angle of contact (pure water) becomes 5 degrees.

Thereafter, the exposure region of 20 μm×100 μm (the direction spanning 100 μm corresponds to the axial direction of the lamp) was ink jet coated with 10 pl of silver nano ink (water based solvent), and the linewidth at the center portion was measured with the use of an optical microscope. The results are shown in Table 2.

TABLE 2

| | Oxygen 20 kPa | | | |
|---|---|---|---|---|
| | Gap 20 μm Linewidth [μm] | | Gap 5 μm Linewidth [μm] | |
| SAM | SFL | Excimer | SFL | Excimer |
| octadecyltrimethoxysilane | 20.4 | 23.6 | 20.3 | 21.1 |
| octadecyltrichlorosilane | 20.3 | 23.2 | 20.2 | 21.0 |
| tridecafluorooctyltrimethoxysilane | 21.1 | 24.1 | 20.5 | 21.4 |
| octadecylphosphonic acid | 20.5 | 23.5 | 20.3 | 21.0 |
| perfluorooctylphosphonic acid | 20.9 | 23.8 | 20.6 | 21.4 |
| hexadecanethiol | 21.3 | 24.4 | 20.9 | 21.6 |

As shown in Table 2, in patterning in an atmosphere containing oxygen, when the SFL that emits the VUV light having a continuous spectrum in a range where the wavelength ranges from 180 nm to 200 nm is used as a light source, the pattern formed in the SAM has a linewidth that is substantially equivalent to the mask size (20 μmL/S). In this manner, it was confirmed that, by using the SFL having a continuous spectrum in a range where the wavelength ranges from 180 nm to 200 nm as the light source, a pattern that accurately follows the mask pattern can be obtained with high accuracy, as compared to a case in which an excimer lamp is used as the light source.

It was also confirmed that, when the SFL is used, high pattern accuracy is obtained in either of the cases in which the gap is 20 μm and the gap is 5 μm (a change in the pattern accuracy associated with the size of the gap is small). In other words, it was confirmed that, when the SFL is used, a gap dependence (a change in the pattern accuracy associated with the gap) is small, as compared to a case in which an excimer lamp is used.

In this manner, it was confirmed that, when an organic monolayer, such as a SAM, is irradiated with the VUV light and patterned, favorable patterning can be achieved by irradiating the organic monolayer with the VUV light having a continuous spectrum in a range where the wavelength ranges from 180 nm to 200 nm.

EXAMPLE 3

First, a $SiO_2$ film was laminated on a Si substrate, which was then left for approximately one month to allow $CO_2$ to adhere to the $SiO_2$ surface; thus, a pattern forming substrate having hydrophobicity was fabricated. Next, this pattern forming substrate was irradiated with vacuum ultraviolet radiation by using, as a light source, a short-arc flash lamp (SFL) illustrated in FIG. 4 and an excimer lamp, and patterning was carried out. Thereafter, the accuracy of the obtained pattern was evaluated.

As the SFL, one in which the interelectrode distance is 3 mm and the arc tube is filled with xenon gas (Xe) at a filling pressure of 5 atm was used. This SFL was powered at 10 Hz by charged energy (3.24 J) of a capacitor having a capacitance of 18 μF charged at 600 V.

As the excimer lamp, a double-pipe excimer lamp in which the arc tube is filled with xenon gas (Xe) at a filling pressure of 0.5 atm was used. The arc tube having a diameter of φ20 mm and a length of 80 mm in the direction of the tube axis was used. The excimer lamp was powered at 100 W.

(Patterning Method)

The pattern forming substrates were disposed directly underneath the centers of the respective lamps at a distance of 40 mm and were exposed via a mask. The mask was disposed over the pattern forming substrate with one of three types of gaps of 0 μm, 20 μm, and 40 μm provided therebetween, with the use of L/S=4/4 [μm] and L/S=2/2 [μm]. The space between the lamp and the mask was purged with nitrogen, the atmosphere of the gap (the space between the mask and the pattern forming substrate) was the air (oxygen at approximately 20 kPa), and the exposure was carried out for two minutes.

Thereafter, a SAM was formed through a gas-phase process, a fluorescent dye TAMRA (Tetramethylrhodamine) was modified, and the exposure region was measured with the use of a fluorescence microscope.

When the $SiO_2$ surface to which $CO_2$ has adhered is irradiated with the VUV light via a mask, C on the $SiO_2$ surface is partially removed, and the region irradiated with the VUV light is hydrophilized; thus, a hydrophilized pattern of the $SiO_2$ film is obtained. Then, by coating the $SiO_2$ film with a SAM that can adhere only to the hydrophilization processed portion of the $SiO_2$ film, a pattern of the SAM is obtained. However, the SAM itself is transparent and invisible, and thus the SAM is modified with a fluorescent dye TAMRA after the SAM is laminated, and the SAM is thus visualized.

Figure 7:
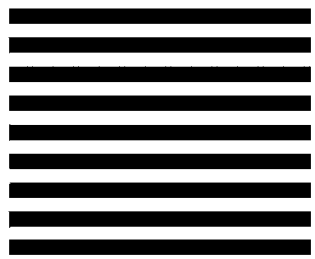
FIG. 7 is a view showing a measurement result of a substrate on which a patterning is applied by the SFL.
Figure 8:
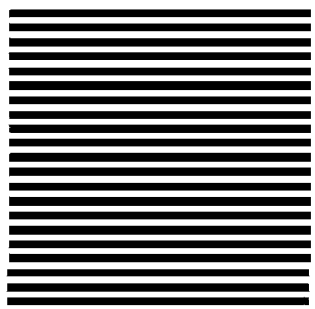
FIG. 8 is a view showing the measurement result of the substrate on which the patterning is applied by the SFL.

FIG. 7 illustrates the result of observing, with a fluorescence microscope, the substrate patterned by the SFL with the use of a mask of L/S=4/4 [μm]. FIG. 8 illustrates the result of observing, with a fluorescence microscope, the substrate patterned by the SFL with the use of a mask of L/S=2/2 [μm]. As illustrated in FIGS. 7 and 8, it can be seen that sharp patterns were obtained for both L/S=4/4 [μm] and 2/2 [μm]. On the other hand, when an excimer lamp was used as a light source, resolution was obtained for neither L/S=4/4 [μm] nor 2/2 [μm]

In this manner, it was confirmed that, when a substrate having an admolecular layer containing carbon on the surface thereof, such as a $SiO_2$ film to which $CO_2$ has adhered, is irradiated with the VUV light and patterned, favorable patterning can be achieved by irradiating the substrate with the VUV light having a continuous spectrum in a range where the wavelength ranges from 180 nm to 200 nm.

(Modifications)

Although a case in which a short-arc flash lamp is employed as a light source has been described in the foregoing embodiments, it suffices that the VUV light emitted by a light source have a continuous spectrum in a range where the wavelength ranges from 180 nm to 200 nm, and a light source of various configurations can be used as a light source. Here, it suffices that the VUV light emitted by the light source have a continuous spectrum in a range where the wavelength ranges from 180 nm to 200 nm, and it is not necessary that there be a peak in the range where the wavelength ranges from 180 nm to 200 nm.

Even in a case in which a point light source is employed as the light source, the light source is not limited to a short-arc flash lamp, and a light source of various configurations can be used as the light source. For example, the light source is not limited to a flash lamp, and a short arc lamp that has a short interelectrode distance of approximately 1 to 10 mm and emits light through an arc discharge can also be employed.

Furthermore, in the foregoing embodiments, when the illuminance distribution of the VUV light with which the workpiece W is irradiated needs to be uniform, for example, the light irradiation apparatus 100 may be configured as follows.

The paraboloid mirror 12 in the vacuum ultraviolet radiation source device 10 is replaced by an ellipsoid condenser mirror, and the light-emitting unit of the SFL 11 is disposed at a first focal point of the ellipsoid condenser mirror. An integrator is disposed at a second focal point at which light that exits through the window portion 14 is condensed, the light from the integrator is collimated by a collimator lens or a collimator mirror, and the mask M is irradiated with that light.

The integrator and the collimator lens or the collimator mirror are disposed in an optical path through which the light that is emitted by the vacuum ultraviolet radiation source device 10 and with which the workpiece W is irradiated travels, and thus the integrator, the collimator lens, and the collimator mirror are formed of a material having a high light-transmitting property in the VUV range.

Although specific embodiments are described above, these embodiments are merely illustrative in nature and are not intended to limit the scope of the present invention. The apparatuses and the methods described in the present specification can be implemented in embodiments aside from those described above. Omissions, substitutions, and modifications can be made, as appropriate, to the embodiments described above without departing from the scope of the present invention. An embodiment with such omissions, substitutions, and modifications is encompassed by what is described in the claims and any equivalent thereof and falls within the technical scope of the present invention.

INDUSTRIAL APPLICABILITY

According to the method of manufacturing the pattern forming substrate according to the present invention, a pattern forming substrate can be irradiated with vacuum ultraviolet radiation with less optical absorption by oxygen, and thus generation of ozone when the pattern forming substrate is irradiated with the vacuum ultra violet light can be reduced. Accordingly, a pattern that accurately follows a mask pattern can be formed in the pattern forming substrate with high accuracy, which is thus useful.

REFERENCE SIGNS LIST

10: vacuum ultra violet light source device
11: flash lamp (SFL)

12: paraboloid mirror
13: lamp housing
14: window portion
15: feeder unit
21: enclosing member
21a: gas introduction port
21b: discharge port
22: mask stage
23: work stage
24: enclosing member
24a: gas introduction port
24b: discharge port
31: control unit
32: stage moving mechanism
111a: arc tube
111b: first sealing tube
111c: second sealing tube
112: sealing glass tube
113a: first main electrode (anode)
113b: second main electrode (cathode)
114a and 114b: electrode rods
115a and 115b: trigger electrodes
116a and 116b: inner leads
117a and 117b: outer leads
118a and 118b: metal foils
119: supporter member
120: sparker electrode
M: mask
W: workpiece

What is claimed is:

1. A method for manufacturing a patterned object, comprising:
irradiating a pattern forming substrate with light containing vacuum ultra violet light in an atmosphere containing oxygen via a mask on which a prescribed pattern is formed; and
manufacturing a patterned object in which a pattern is formed including a modified portion and non-modified portion on a light irradiation surface of the pattern forming substrate,
the vacuum ultra violet light being light having a continuous spectrum in a range where a wavelength ranges from 180 nm to 200 nm, and
the vacuum ultra violet light has one or more peaks in the continuous spectrum,
wherein an illuminance of the vacuum ultra violet light in the range where the wavelength ranges from 180 nm to 200 nm is equal to or greater than an illuminance in a range where the wavelength ranges from 160 nm to 180 nm.

2. The method for manufacturing a patterned object according to claim 1, wherein the pattern forming substrate is a substrate composed of an aliphatic compound polymer.

3. The method for manufacturing a patterned object according to claim 2, wherein the pattern forming substrate is a substrate composed of cyclic olefin polymer (COP) or a cyclic olefin copolymer (COC) that is a copolymer of the COP.

4. The method for manufacturing a patterned object according to claim 1, wherein the pattern forming substrate is a substrate in which a self-assembled monolayers (SAM) is formed on a surface of the pattern forming substrate, and
the patterned object is manufactured by irradiating the SAM on this pattern forming substrate with the vacuum ultra violet light and removing a portion of the SAM in a patterned shape.

5. The method for manufacturing a patterned object according to claim 1, wherein an inorganic layer containing carbon is formed on the pattern forming substrate.

6. The method for manufacturing a patterned object according to claim 1, wherein the pattern forming substrate is a substrate having a layer made of an organic-inorganic hybrid material provided on a surface of the substrate.

7. A patterned object manufactured by the method for manufacturing a patterned object according to claim 1.

8. A light irradiation apparatus, comprising:
a mask stage arranged apart from the pattern forming substrate and configured to hold a mask on which a prescribed pattern is formed;
a vacuum ultra violet light source unit configured to irradiate the pattern forming substrate with vacuum ultra violet light via the mask; and
an atmosphere controlling unit configured to set a space between the mask and the pattern forming substrate to be an atmosphere containing oxygen,
the vacuum ultra violet light source unit irradiating light, as the vacuum ultra violet light, having a continuous spectrum in a range where a wavelength ranges from 180 nm to 200 nm and having one or more peaks in the continuous spectrum,
wherein an illuminance of the vacuum ultra violet light in the range where the wavelength ranges from 180 nm to 200 nm is equal to or greater than an illuminance in a range where the wavelength ranges from 160 nm to 180 nm.

* * * * *